US012636239B2

(12) United States Patent
Kim et al.

(10) Patent No.: US 12,636,239 B2
(45) Date of Patent: May 26, 2026

(54) HYDROQUINONE STABILIZING COMPOSITION

(71) Applicants: LG HOUSEHOLD & HEALTH CARE LTD., Seoul (KR); TAI GUK PHARM. IND. CO., LTD., Buyeo-gun (KR)

(72) Inventors: Mi-Na Kim, Seoul (KR); Seung-Hyun Jun, Seoul (KR); Hyun-Min Hwang, Seoul (KR); Na-Eun Yook, Seoul (KR); Mun-Ju Shin, Seoul (KR); Seo-Hun Roh, Buyeo-gun (KR)

(73) Assignees: LG HOUSEHOLD & HEALTH CARE LTD., Seoul (KR); TAI GUK PHARM. IND. CO., LTD., Buyeo-gun (KR)

( * ) Notice: Subject to any disclaimer, the term of this patent is extended or adjusted under 35 U.S.C. 154(b) by 318 days.

(21) Appl. No.: 18/004,329

(22) PCT Filed: Jun. 18, 2021

(86) PCT No.: PCT/KR2021/007699
§ 371 (c)(1),
(2) Date: Jan. 5, 2023

(87) PCT Pub. No.: WO2022/010129
PCT Pub. Date: Jan. 13, 2022

(65) Prior Publication Data
US 2023/0277425 A1 Sep. 7, 2023

(30) Foreign Application Priority Data

Jul. 8, 2020 (KR) ........................ 10-2020-0084277
May 26, 2021 (KR) ........................ 10-2021-0067884

(51) Int. Cl.
| | |
|---|---|
| *A61K 8/34* | (2006.01) |
| *A61K 8/86* | (2006.01) |
| *A61K 31/05* | (2006.01) |
| *A61Q 19/02* | (2006.01) |

(52) U.S. Cl.
CPC ................ *A61K 8/347* (2013.01); *A61K 8/86* (2013.01); *A61K 31/05* (2013.01); *A61Q 19/02* (2013.01); *A61K 2800/52* (2013.01)

(58) Field of Classification Search
CPC ...... A61K 8/347; A61K 8/86; A61K 2800/52; A61Q 19/02
See application file for complete search history.

(56) References Cited

U.S. PATENT DOCUMENTS

| | | | |
|---|---|---|---|
| 8,709,385 | B2 | 4/2014 | Tamarkin et al. |
| 2002/0155089 | A1* | 10/2002 | Chowdhary ............ A61P 35/00 |
| | | | 604/20 |

| | | | |
|---|---|---|---|
| 2003/0053968 | A1* | 3/2003 | Wortzman ............. A61K 45/06 |
| | | | 514/474 |
| 2006/0140888 | A1 | 6/2006 | Ohashi et al. |
| 2007/0166251 | A1 | 7/2007 | Dayan et al. |
| 2010/0249240 | A1* | 9/2010 | Meadows ............... A61P 23/02 |
| | | | 514/626 |
| 2013/0287825 | A1 | 10/2013 | Roy et al. |
| 2014/0243423 | A1 | 8/2014 | Gurge et al. |
| 2016/0128944 | A1* | 5/2016 | Chawrai ................ A01N 25/34 |
| | | | 514/159 |

FOREIGN PATENT DOCUMENTS

| | | |
|---|---|---|
| CN | 108578261 A | 9/2018 |
| EP | 1 562 531 B1 | 1/2016 |
| JP | 61-227516 A | 10/1986 |
| KR | 10-2009-0114621 A | 11/2009 |
| KR | 10-2015-0066805 A | 6/2015 |
| KR | 10-2017-0095466 A | 8/2017 |

OTHER PUBLICATIONS

Mustafa "(Evolution in Enhancement Oral Bioavailability of Atorvastatin and Stability of Hydroquinone Topical Gel) Based on Microemulsion Phase Behavior of Tri-Block Co-polymer: Poloxamer 188" M.Sc. Thesis, 2013 (Year: 2013).*
Mustafa. "(Evolution in Enhancement Oral Bioavailability of Atorvastatin and Stability of Hydroquinone Topical Gel) Based on Microemulsion Phase Behavior of Tri-Block Co-polymer: Poloxamer 188" M.Sc. Thesis, Al-Quds University, 2013. (Year: 2013).*
The Notice of Refusal (translated) for corresponding JP Patent Appl No. 2023-501400, issued Jan. 29, 2024, 8 pages.
Cataloging in Publication (CIP) Data, Practical Dispensing Science / Edited by Shao Zhigao, Nanjing: Southeast. University Press, Nov. 2013. Community Pharmacy Professional Position Training Textbook, ISBN. 978-7-5641-4620-7, China National Library CIP Data No. (2013) 267774.

* cited by examiner

*Primary Examiner* — Ali Soroush
*Assistant Examiner* — Rajan Pragani
(74) *Attorney, Agent, or Firm* — Vorys, Sater, Seymour and Pease LLP; Mih Suhn Koh

(57) ABSTRACT

Provided in the present disclosure is a composition comprising hydroquinone or a derivative thereof as an active ingredient, and characterized in that the hydroquinone or the derivative thereof is stabilized by means of poloxamer. The composition of the present disclosure increases the soluble concentration of the hydroquinone or the derivative thereof, can have high melt stability without precipitation even at high concentration in water, can enhance storage stability by preventing oxidation reaction to external stimulations such as heat, oxygen and light, can prevent discoloration, and thus has reduced toxicity induced by an oxidation product of the hydroquinone and can reduce inflammatory response. Also, the composition of the present disclosure can enhance whitening efficacy by enhancing the skin permeability of the hydroquinone or the derivative thereof by means of micelles, and thus is useful for a whitening activity having hydroquinone or a derivative thereof as an active ingredient.

13 Claims, 5 Drawing Sheets

【Figure 1】
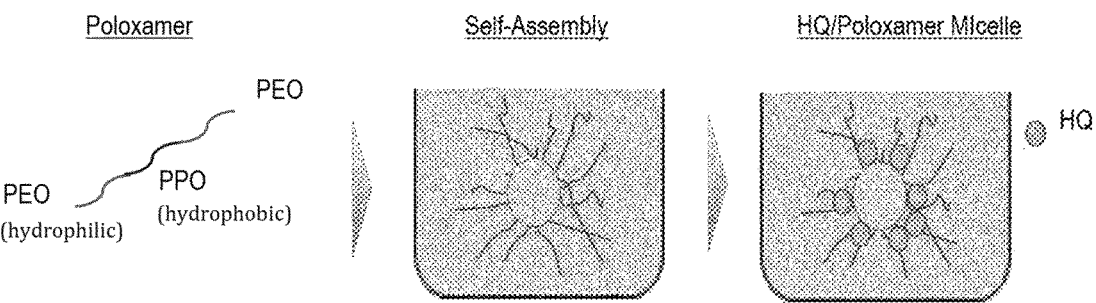
【Figure 2】
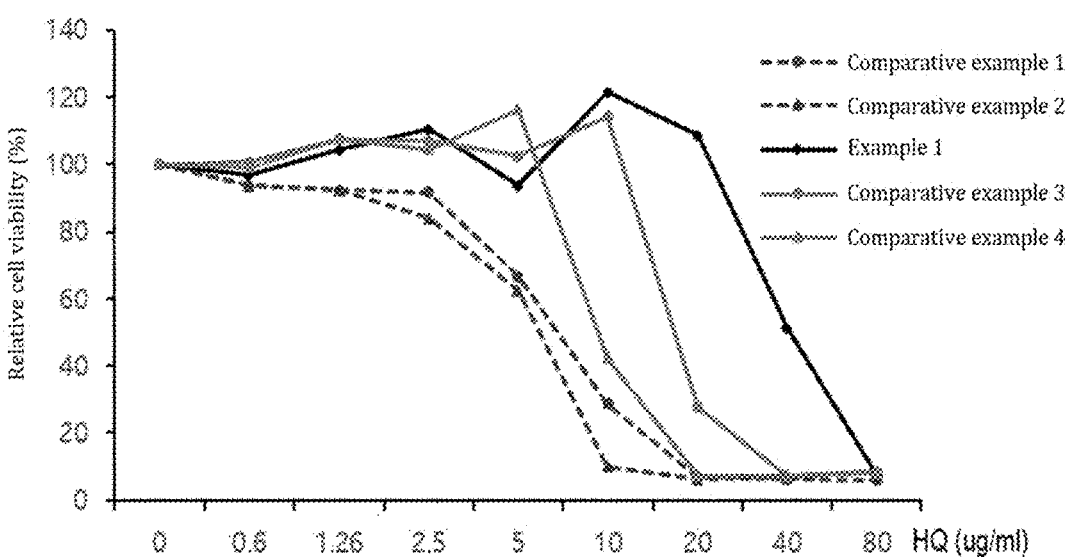

【Figure 3】
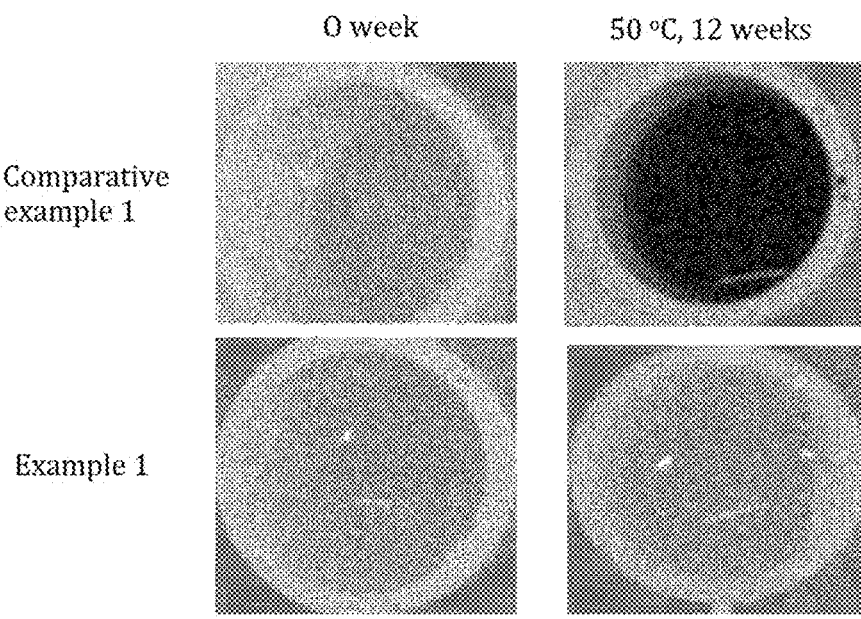
【Figure 4】
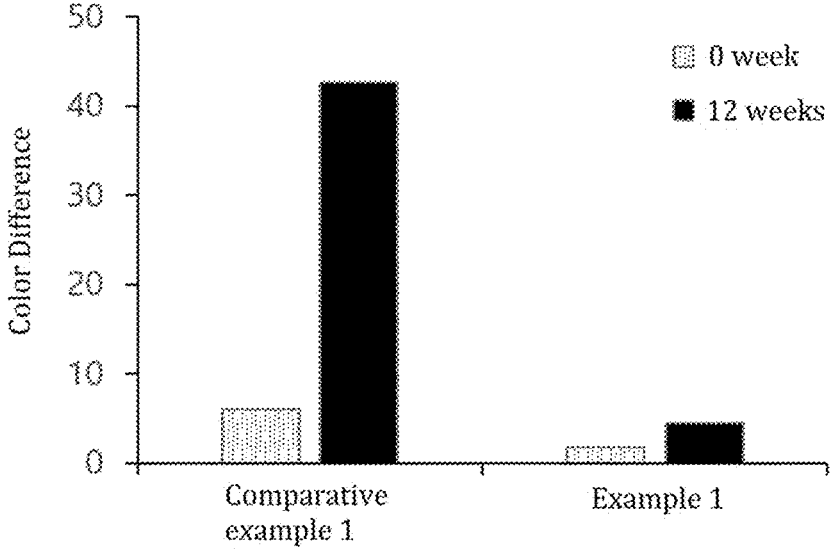

【Figure 5】
Comparative example 1        Example 1
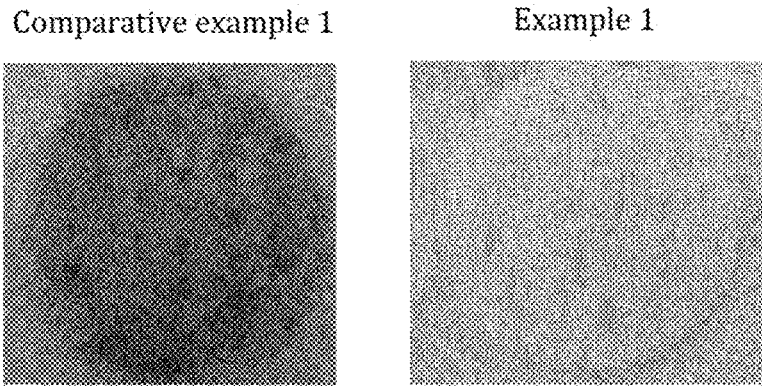
After application to pig skin
【Figure 6】
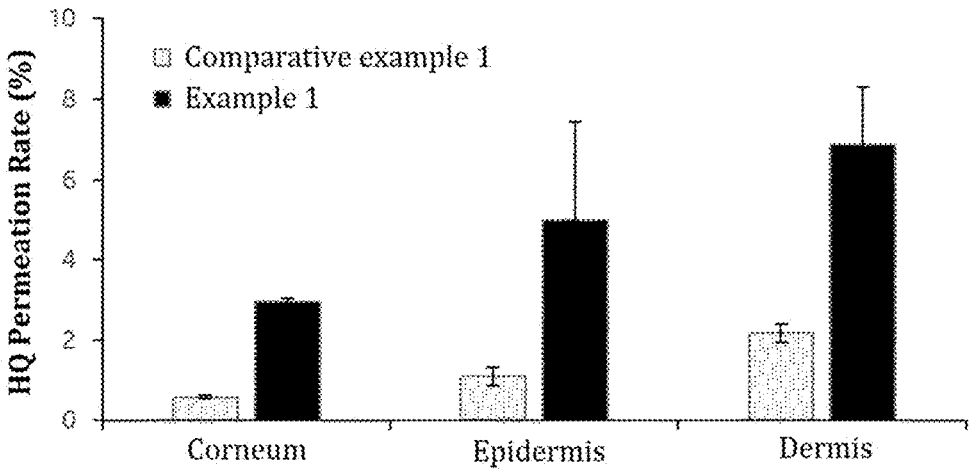

【Figure 7】
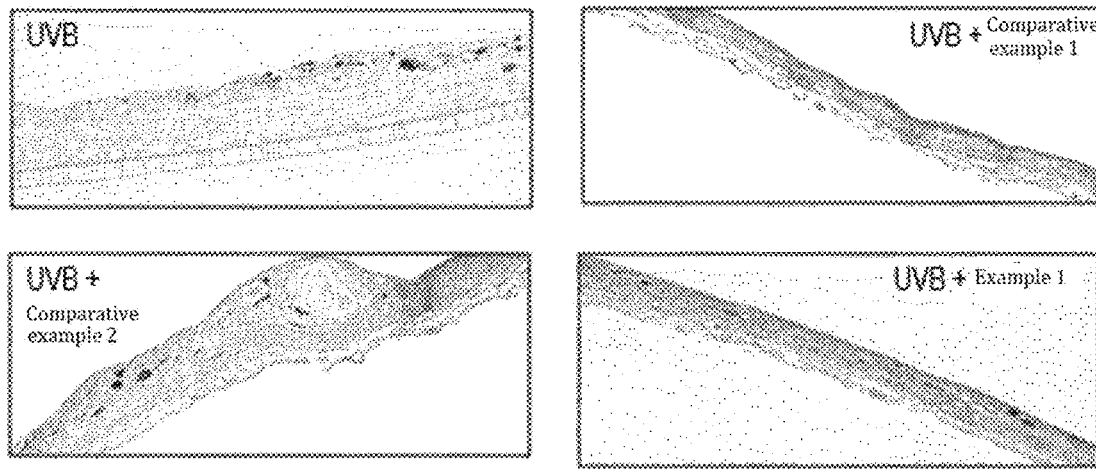
【Figure 8】
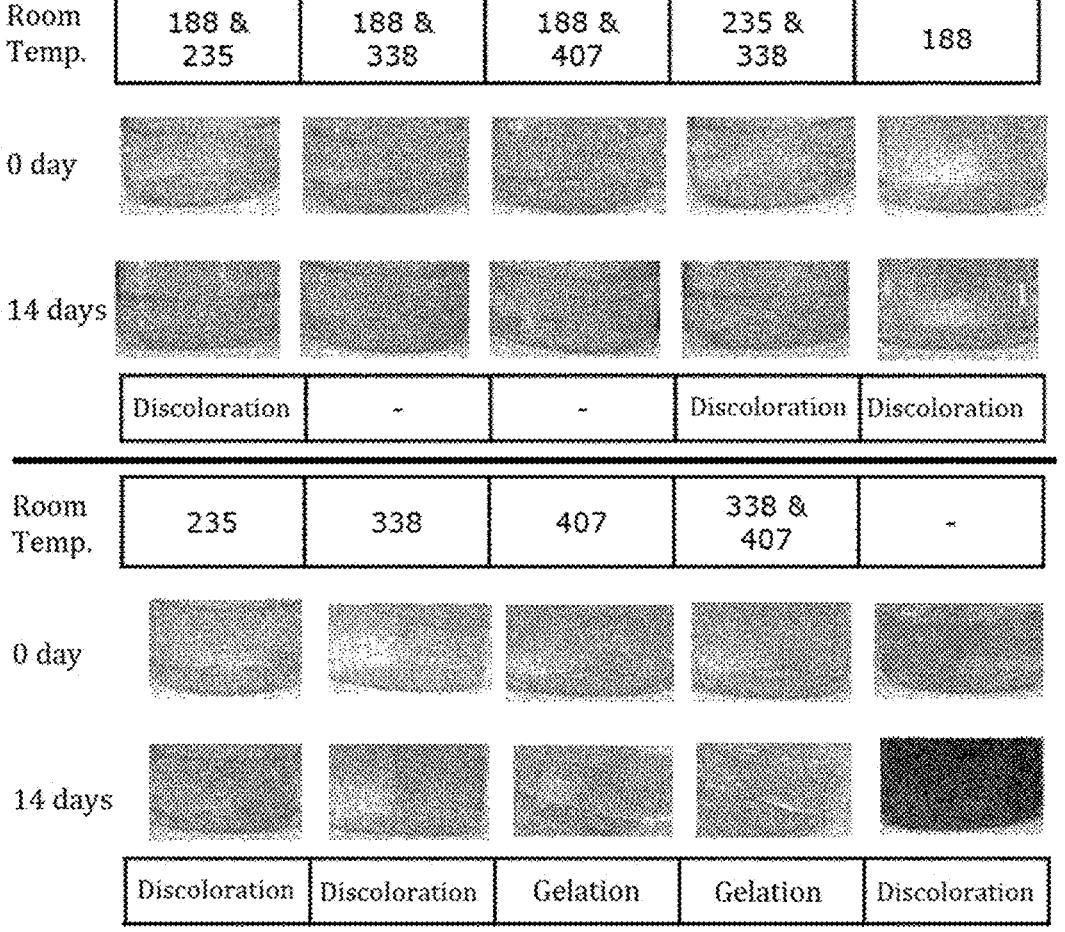
| Room Temp. | 188 & 235 | 188 & 338 | 188 & 407 | 235 & 338 | 188 |
|---|---|---|---|---|---|
| 0 day | | | | | |
| 14 days | | | | | |
| | Discoloration | ~ | ~ | Discoloration | Discoloration |
| Room Temp. | 235 | 338 | 407 | 338 & 407 | ~ |
|---|---|---|---|---|---|
| 0 day | | | | | |
| 14 days | | | | | |
| | Discoloration | Discoloration | Gelation | Gelation | Discoloration |

【Figure 9】
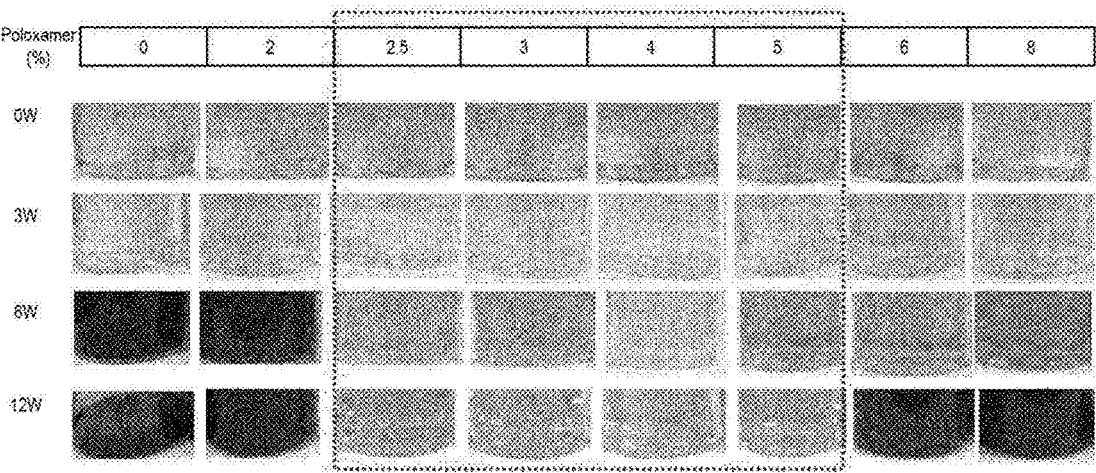

HYDROQUINONE STABILIZING COMPOSITION

TECHNICAL FIELD

This application claims priority to Korean Patent Application No. 10-2020-0084277 filed on Jul. 8, 2020 and Korean Patent Application No. 10-2021-0067884 filed on May 26, 2021, the entire contents of which are incorporated herein by reference.

The present invention relates to a composition comprising hydroquinone or a derivative thereof as an active ingredient. More specifically, it relates to a composition having maximized whitening effect with minimized skin side effects and increased skin permeability.

BACKGROUND ART

Skin is an important tissue for protecting the human body and is largely divided into epidermis, dermis, and subcutaneous tissue. Melanin produced by melanocytes present in the basal layer of the epidermis, absorbs light energy and thus protects organs beneath the dermis from damage caused by UV. However, when melanin is accumulated by excessive melanin synthesis or insufficient keratinization due to increased exposure to ultraviolet rays by environmental pollution or due to aging, the deposited pigment causes spots and freckles, and thus the skin color is darkened.

In order to prevent the pigmentation, kojic acid, vitamin C (L-ascorbic acid), glutathione, and the like have been generally used in the conventional cosmetics field. However, the whitening effects thereof are not sufficient. On the other hand, hydroquinone has an excellent whitening effect unlike the above ingredients, but has a problem of being easily discolored due to oxidation by air or light. The oxidized hydroquinone is changed into quinhydrone via p-benzoquinone, and it is known that they have cytotoxicity and are carcinogenic and allergenic.

Due to these problem, many countries regulate the use of hydroquinone in limited concentration, and conventionally, airtight light-shielding containers have been used to prevent the oxidation of hydroquinone. However, the exposure to oxygen or light could not avoid if product is opened. For this reason, the methods of reducing the oxidation of hydroquinone, such as adjusting the pH to around 4 or applying various antioxidants (e.g., ascorbic acid) has been reported. However, it has been reported that the hydroquinone ointments containing ascorbic acid as an antioxidant cause skin allergy, and the antioxidant itself may be discolored when vitamin E or ascorbic acid is used as an antioxidant.

On the other hand, the use of dimethyl isosorbide (DMI) as a skin permeation enhancer is known as the technique for increasing the skin permeability of hydroquinone, but this technique have the problem of causing discoloration of hydroquinone at high temperature.

DISCLOSURE

Technical Problem

Therefore, the problem to be solved by the present invention is to provide a hydroquinone composition with the increased skin permeability and oxidation stability of hydroquinone.

Another problem to be solved by the present invention is to provide a composition comprising hydroquinone as an active ingredient, with formulation stability as well as the skin permeability and the oxidation stability.

Other problem to be solved by the present invention is to provide a composition having minimized skin side effects and maximized skin whitening effect due to the above advantages.

Technical Solution

In order to solve the above problem, the present disclosure provides a composition comprising hydroquinone or a derivative thereof as an active ingredient, wherein the hydroquinone or a derivative thereof is stabilized by using poloxamer.

One embodiment of the present disclosure also provides a composition comprising hydroquinone or a derivative thereof as an active ingredient, wherein the hydroquinone or a derivative thereof is stabilized by using poloxamer, and wherein the composition has further improved oxidation stability of the active ingredient and formulation stability by using two or more poloxamers.

The present inventors completed the present invention by confirming that the composition may have the increased content of stabilized hydroquinone or its derivative with improved skin permeability when the hydroquinone or its derivative is placed inside or around micelles formed with the poloxamer. In addition, one aspect of the present invention was completed by confirming that the composition may have the further improved stability of hydroquinone or its derivative and have the improved formulation stability by preventing gelation and the like even in an external aqueous phase environment when the composition has a three-component mixture (hydroquinone or a derivative thereof and two poloxamers) in which two or more poloxamers are different in the hydrophilic block length. It is thought that the three-component mixture of the present disclosure can prevent gelation by steric hindrance and that the hydroquinone can be efficiently entrapped in the entangled spaces of hydrophilic blocks, but the present disclosure is not limited to such theory.

Therefore, one embodiment of the present disclosure provides a composition having minimized skin side effects due to prevention of discoloration by oxidation or light and having increased skin permeability wherein one or more types of block copolymer poloxamers form micelles by self-assembly and the hydroquinone entrapped in the micelles. Another embodiment of the present disclosure provides a composition comprising hydroquinone or a derivative thereof as an active ingredient, wherein the composition comprises the micelles formed with one or more (preferably, two or more) poloxamer, and wherein the external phase containing the micelles is water phase.

In the present disclosure, as the active ingredient, hydroquinone or a derivative thereof may be at least one selected from the group consisting of hydroquinone, hydroquinone monobenzyl ether, hydroquinone monomethyl ether and hydroquinone monoethyl ether. Preferably, hydroquinone can be used.

Hydroquinone or a derivative thereof is preferably contained in the amount of 0.1 to 10% by weight, preferably 0.5 to 8% by weight, more preferably 1 to 5% by weight, based on the total weight of the composition. When contained in the amount of 10% by weight or more, hydroquinone not entrapped in micelles may be oxidized or present outside, which may cause discoloration.

In the present disclosure, the poloxamer may be a tripolymer composed of PEO-PPO-PEO, for example poloxamer 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, 407, etc. (The first two digits of the three-digit number in the poloxamer name mean the approximate value of dividing the molecular weight (g/mol) of PPO by 100, and the last one digit means the value of dividing the percentage of PEO content in poloxamer by 10).

In the present disclosure, the term "about" or "approximately" means±20% of the value, preferably ±10% of the value.

In the present disclosure, the poloxamer is preferably contained in the amount of 0.1 to 40% by weight based on the total weight of the composition. For example, the poloxamer can be contained in the amount of 0.1 to 20% by weight, more preferably 0.5 to 10% by weight, and even more preferably 2.5 to 5% by weight based on the total weight of the composition. However, the minimum content of poloxamer should be sufficient to form micelles. When the content of poloxamer is too small, the prepared amount of micelles may be insufficient to entrap hydroquinone, and when the content is too high, gelation may occur.

Unlike the preparation of liposomes or nanoemulsions which require the separate process such as high-pressure emulsification, the poloxamer of the present disclosure does not require special process and can be manufactured through self-assembly, which is more efficient solubilization and micelle formation method in terms of productivity.

Preferably, the composition according to one embodiment of the present disclosure preferably comprises two or more poloxamers as the poloxamer. One of the two poloxamers (the first poloxamer) is a poloxamer having the PPO molecular weight of about 1200-1800 g/mol and the PEO content percentage of about 30-80%, preferably 40-80% (e.g., poloxamers 188, 185, 124, 184, etc.). The other poloxamer (second poloxamer) is a poloxamer having the PPO molecular weight of about 3000-4500 g/mol and the PEO content percentage of about 30-80%, preferably 40-80% (e.g., poloxamer 338, 407, 334, 335, etc.). When two poloxamers with different properties are mixed, it is more preferable in terms of preventing gelation of the formulation as well as preventing oxidation of hydroquinone.

More preferably, the composition according to one embodiment of the present disclosure comprises the poloxamer having the molecular weight of polyoxypropylene of about 1800 g/mol and the content of polyoxyethylene of about 80% by weight (e.g., poloxamer 188), and comprises the poloxamer having the molecular weight of polyoxypropylene of about 3300 g/mol and the content of polyoxyethylene of about 80% by weight (e.g., poloxamer 338) and/or the poloxamer having the molecular weight of polyoxypropylene of about 4000 g/mol and the content of polyoxyethylene of about 70% by weight (e.g., poloxamer 407). That is, a preferred composition according to one embodiment of the present disclosure comprises a combination of poloxamers 188 and 338, a combination of poloxamers 188 and 407, or a combination of poloxamers 188, 338 and 407.

When the first poloxamer and the second poloxamer are used, the weight ratio of the mixture may be 1:0.1 to 10, preferably 1:0.2 to 5, and more preferably 1:0.8 to 1.2.

In another embodiment of the present disclosure, when a combination of poloxamers is used, for example, the first poloxamer and the second poloxamer may be mixed in a weight ratio of 1:0.01 to 1. More preferably, in term of various purposes of the present invention, the first poloxamer is used in the equal or relatively smaller amount.

The composition according to the present disclosure may further include an antioxidant to further improve the stability of hydroquinone or a derivative thereof. Antioxidant(s) are used to further enhance the improved storage stability of hydroquinone entrapped in micelles, and may be one or more selected from sodium bisulfite, sodium sulfite, vitamin C and its derivatives, vitamin E and its derivatives, and dibutylhydroxytoluene (BHT), ethylenediaminetetraacetic acid (EDTA), and glutathione. If used, the antioxidant is preferably contained in the amount of 0.05 to 15% by weight, more preferably 0.1 to 10% by weight, based on the total weight of the composition. The use of excessive amount of antioxidants may cause discoloration of the antioxidants themselves, or cause phase separation of the micelles produced with block copolymers. However, since the antioxidant comprised in the composition of the present invention is used to further improve the stability of hydroquinone or a derivative thereof, the addition of the antioxidant is optional.

In addition to the above components, the composition according to the present disclosure may comprise water and a hydrophilic solvent as a material for dissolving hydroquinone or a derivative thereof, and these components can be comprised in the remained amount except for the hydroquinone or derivative thereof, poloxamer and antioxidant.

The hydrophilic solvent may be a polyhydric alcohol or a volatile organic solvent. Specifically, it may be polyethylene glycol, propylene glycol, dipropylene glycol, glycerin, 1,3-butanediol, isopropyl alcohol, ethanol and the like, but are not limited thereto. Preferably, it may be preferably isopropyl alcohol and/or ethanol. The hydrophilic solvent may be used in the amount of 5 to 50% by weight based on the total weight of the composition. Although the use of a hydrophilic solvent is not essential in the present invention, the storage stability of hydroquinone or its derivatives may be increased and the micelles may be more easily formed when the hydrophilic solvent used.

The composition according to the present disclosure may be a liquid composition having an external aqueous phase, but also may be a solidified or powdered form by lyophilization or spray drying. Since the solidified or powdered composition is dispersed in an aqueous phase before use, the solidified composition also needs formulation stability of the composition of the present disclosure.

Since the composition of the present disclosure includes hydroquinone or a derivative thereof as an active ingredient, it may be a composition for improving whitening. In yet another embodiment of the present disclosure, the composition of the present disclosure may be a composition for applying to the skin. A composition of the present disclosure may be a pharmaceutical composition or a cosmetic composition.

The composition of the present disclosure may be prepared as a cosmetic or pharmaceutical composition according to conventional manufacturing methods used in the field of cosmetics or pharmaceuticals. Accordingly, the composition of the present invention can be formulated in the form of skin, serum, gel, lotion, cream, powder, patch, etc. and applied in various ways, and when applied to the skin, it can provide the whitening effect.

Preferably, all ingredients described in the present invention do not exceed the maximum limit of use stipulated by relevant laws and regulations of Korea, China, The United States of America, Europe, Japan, etc. (for example, Regulations on the Safety Standards, etc. of Cosmetics (Korea), Safety and Technical Standards for Cosmetics (China), Hygiene Law (China), etc.). That is, preferably, the cosmetic composition according to the present invention contains the ingredients according to the present invention within the content limit permitted by the relevant laws and regulations of each country.

Advantageous Effects

The present disclosure provides a composition comprising hydroquinone or a derivative thereof, characterized in that the composition has the increased solubilization concentration of hydroquinone or its derivative; has high dissolution stability without precipitation even at high concentrations in the aqueous phase; has the increased storage stability by preventing oxidation due to external stimulations such as heat, oxygen, or light and by preventing discoloration; thereby reduces toxicity and inflammation caused by the oxidized products of hydroquinone. In addition, the composition of the present disclosure comprising hydroquinone or a derivative thereof as an active ingredient is useful for improving whitening effect because of the improved skin permeability of hydroquinone or its derivative through micelles.

BRIEF DESCRIPTION OF DRAWINGS

FIG. 1 is a schematic diagram of micelles in which hydroquinone is entrapped by poloxamer, a triblock copolymer composed of hydrophobic polyoxypropylene in the center and hydrophilic polyoxyethylene on both sides.

FIG. 2 is the experimental result showing the reduction in cytotoxicity of the stabilized hydroquinone.

FIG. 3 is the photographs of the experimental result showing the reduction in discoloration of the stabilized hydroquinone.

FIG. 4 is the test result of color difference showing the reduction in discoloration of the stabilized hydroquinone.

FIG. 5 is the result of applying Example 1 and Comparative Example 2 to pig skin.

FIG. 6 is the experimental result showing the increased skin delivery of the stabilized hydroquinone.

FIG. 7 is the result of confirming the change in melanin on the sectioned plane 3 days after applying Example 1, Comparative Example 1, and Comparative Example 2 to 3D skin.

FIG. 8 is the result showing the effect of the types of poloxamer on the stability and gelation of hydroquinone.

FIG. 9 is the result showing the effect of the contents of poloxamer on the stability of hydroquinone under the severe conditions.

MODE FOR INVENTION

Hereinafter, examples and the like will be described in detail to aid understanding of the present invention. However, the examples according to the present invention can be modified in many different forms, and the scope of the present invention should not be construed as being limited to the following examples. Examples of the present invention are provided to more completely explain the present invention to those skilled in the art.

Formulation or Preparation of Example 1 and Comparative Examples 1 and 2

First, Example 1 according to the present invention, Comparative Example 1, and Comparative Example 2 were prepared according to the composition shown in Table 1 below.

TABLE 1

| Component | Material (Unit: weight %) | Example 1 | Comparative Example 1 or 2 |
|---|---|---|---|
| Block copolymer 1 (First poloxamer) | Poloxamer 188 | 10 | 0 |
| Block copolymer 2(Second poloxamer) | Poloxamer 338 | 10 | 0 |
| Antioxidant | Sodium metabisulfite | 0.5 | 0 |
| Hydrophilic solvent | Dipropylene glycol | 6.6 | 6.6 |
| Active ingredient | Hydroquinone | 4 | 4 |
| | Distilled water | up to 100 | up to 100 |

Example 1 is the composition comprising hydroquinone entrapped in the block copolymers. Comparative Example 1 is the composition comprising hydroquinone not entrapped in a block copolymer. Comparative Example 2 is the composition which comprises not entrapped hydroquinone and is discolored at 50° C. for 12 weeks.

Specifically, it was prepared as follows: Block copolymer 1 was added to a certain amount of distilled water according to the ratio shown in Table 1 while maintaining at 50~60° C. After stirring at 1000 rpm until block copolymer 1 was completely dissolved, the mixture was cooled to a temperature of 10° C. Block copolymer 2 was slowly added to the cooled solution with stirring at room temperature to form micelles. Thereafter, bubbles were removed by vacuuming with a vacuum pump, and then the antioxidant and the hydrophilic solvent were added with stirring at room temperature. Thereafter, hydroquinone was added with stirring at 1200 rpm to entrap hydroquinone in the micelles (see FIG. 1).

In the Comparative Examples 1 and 2, the hydrophilic solvent and hydroquinone were mixed with stirring at 1000 rpm at room temperature according to the ratio as shown in Table 1 without the block copolymers.

For the Comparative Examples 3 and 4, the commercially available cream comprising hydroquinone was used. The Comparative Examples 2 and 4 were oxidized by storing at 50° C. for 12 weeks in order to evaluate the cytotoxic effect due to oxidation of hydroquinone.

Evaluation Example 1. Measurement of Cytotoxicity of the Stabilized Hydroquinone By adding the compositions of Example 1 and Comparative Examples 1 to 4 to the culture medium of B-16 mouse melanoma cells, the cytotoxicity at the same concentration was measured using CCK-8 kit (Cell Counting Kit-8; Dojindo, Japan). B16 cells were seeded in a 96-well cell culture plate, and then treated so that the concentration of hydroquinone in the composition was 0, 0.6, 1.26, 2.5, 5, 10, 20, 40 and 80 μg/ml. After 48 hours CCK-8 solution was added. After 1 hour, the absorbance of the cell culture medium was measured at 405 nm to measure the cytotoxicity. The results are shown in FIG. 2.

As shown in FIG. 2, when assuming the viability of the untreated control cell group was 100%, the hydroquinone entrapped in the micelles using poloxamer (Example 1) showed 50% of cell viability at the concentration of 40 μg/ml. On the other hand, the hydroquinone dissolved in the aqueous phase without poloxamer (Comparative Examples 1 and 2) showed 40% or less of cell viability at the concentration of 10 μg/ml. In addition, the commercially available hydroquinone cream discolored by oxidation at 50° C. (Comparative Example 4) showed 50% of cell viability at the concentration of 10 μg/ml. These results suggest that the hydroquinone entrapped in the micelles using the poloxamer of the present invention has an effect of reducing toxicity in melanocytes.

Evaluation Example 2. Measurement of Discoloration of Stabilized Hydroquinone The storage stability of Example 1 and Comparative Example 1 compositions was evaluated. After the test samples were stored at 50° C. for 12 weeks, the color difference was calculated. Before and after storage at 50° C. (0, 12 weeks), 100 µl of each composition was added to a 96-well opaque white plate, and then L value (lightness), a value (redness), and b value (yellowness) were measured with Chromameter CR-400 (Minolta, Japan) three times. The overall color difference is expressed as a value of $\Delta E=\sqrt{\Delta L^2+\Delta a^2+\Delta b^2}$. The default value for color difference comparison was the value of the composition wherein the same amounts of hydroquinone and its solvent, water, were placed in a standard plate. The results are shown in FIGS. 3 and 4.

As shown in FIGS. 3 and 4, after 12 weeks at 50° C., the unentrapped hydroquinone of Comparative Example 1 had the higher value of color difference of 42. On the other hand, hydroquinone entrapped with the poloxamer of Example 1 had the color difference of 6, which was the similar value at the $0^{th}$ week of Comparative Example 1. Therefore, it suggests that the storage stability can be increased by entrapping the hydroquinone in the micelles using the poloxamer of the present invention.

Evaluation Example 3. Evaluation of the Skin Delivery of the Stabilized Hydroquinone The skin delivery of Example 1 and Comparative Example 1 compositions was evaluated. A skin permeability test was performed using porcine skin (pig skin) on the test samples. The receptor of the Franz diffusion cell was filled with 50% ethanol, and the porcine skin was placed between the donor and the receptor with the epidermis facing up (toward the donor) and the dermis facing down (toward the receptor). 0.1 ml of Example 1 and Comparative Example 1 compositions were applied to the skin and spread evenly. Thereafter, the skin tissues were recovered after being placed in a thermo-hygrostat for 18 hours. Only the skin tissues exposed to the compositions were used, and the stratum corneum, epidermal, and dermal layers were analyzed separately. For the stratum corneum, the stratum corneum tape (D-Squame standard sampling disc) was separated. The remained pig skin was heated at 70° C. for 15 seconds and then separated into the epidermal and dermal layers, and the hydroquinone present in each tissue layer was dissolved in 50% ethanol. The results are shown in FIGS. 5 and 6.

As shown in FIG. 6, hydroquinone entrapped with the two block copolymers of Example 1 had the skin permeability three times higher than that of Comparative Example 1 in the stratum corneum, epidermal, and dermal layers. It suggests that the hydroquinone-entrapped poloxamer micelles according to the present disclosure can also increase the delivery of hydroquinone to the skin.

Evaluation Example 4. Whitening Effect and Inflammation Evaluation of the Stabilized Hydroquinone in Artificial Skin In order to compare the whitening effect of Example 1 with Comparative Examples 1 and 2, the 3D artificial skin composed of epidermis and melanocytes (Tego Science, Korea) was used. After treating the artificial skin with 50 mJ/cm$^2$ of UVB, 25 µl of each composition was applied to the artificial skin. After culturing for 3 days, the whitening effect was measured by sectioning the 3D skin with a paraffin block, and inflammation was evaluated using the culture medium. The whitening effect was evaluated by the change in the amount of melanin. After staining melanin through Fontana-Masson staining and imaging with a microscope at 40× magnification, the amount of melanin was quantified using the ImageJ program. Inflammation was evaluated using the secretion amount of interleukin 1a, an inflammatory secretion factor, and the secretion amount of interleukin 1a in the culture medium was measured using an ELISA kit (R&D System, USA). Table 2 and FIG. 7 show the inhibitory effect of the melanin formation and inflammation evaluation results in 3D artificial skin.

TABLE 2

| N = 2 (Image 30 spots) | Pigmentation inhibitory effect (vs UVB alone) | Inflammation evaluation (vs HQ 4%) |
|---|---|---|
| UVB | 0 | — |
| UVB + Comparative example 1 | 39.2% * | 100% |
| UVB + Comparative example 2 | 14.9% | 116% |
| UVB + Example 1 | 56.0% ** | 66% |

(* $p < 0.05$,
** $p < 0.005$)

As shown in Table 2 and FIG. 7, in the cases of Comparative Example 1 applied with non-entrapped hydroquinone and Comparative Example 2 applied with the discolored hydroquinone by storing at 50° C., the pigmentation inhibitory effect was approximately 39% and 15%, respectively. On the other hand, the Example 1 in which hydroquinone was stabilized by entrapping with the block copolymers showed a high pigmentation inhibitory effect of 56%. In addition, the result of interleukin 1a, an inflammatory factor, was also reduced by 34% in the case of the stabilized hydroquinone. It suggests that the hydroquinone stabilized in the micelles using the poloxamers of the present invention can increase the skin whitening effect and reduce side effects such as inflammation.

Evaluation of the Effects of Different Types of Poloxamers

The compositions comprising various poloxamers were prepared in the same manner as in Example 1 according to the formulation in Table 3 below.

TABLE 3

| Material (Unit: weight %) | 2 types of poloxamers mixed | 1 type of poloxamer alone |
|---|---|---|
| Poloxamer 1 | 10 | 20 |
| Poloxamer 2 | 10 | — |
| Ascorbic acid | 1 | 1 |
| Dipropylene glycol | 6.6 | 6.6 |
| Hydroquinone | 4 | 4 |
| Distilled water | up to 100 | up to 100 |

Then, after being left at room temperature for 14 days, discoloration and gelation were evaluated, and the results are shown in FIG. 8. As shown in FIG. 8, the least discoloration was observed when poloxamer 188 was used as the first poloxamer and poloxamer 338 or 407 was mixed as the second poloxamer. In addition, when poloxamer 407 was used alone or mixed with poloxamer 338, solubilization was less desirable due to gelation.

Evaluation of Effects According to the Content of Poloxamer

As shown in Table 4 below, the compositions having the same formulation as in Example 1 and changing only the total content of poloxamer to 0-8% were prepared, wherein the first poloxamer (poloxamer 188) and the second poloxamer (poloxamer 338) maintained the weight ratio of 1:1.

TABLE 4

| Material (Unit: wt %) | #1 | #2 | #3 | #4 | #5 | #6 | #7 | #8 |
|---|---|---|---|---|---|---|---|---|
| Poloxamer 1 (Poloxamer 188) | 0 | 1 | 1.25 | 1.5 | 2 | 2.5 | 3 | 4 |
| Poloxamer 2 (Poloxamer 338) | 0 | 1 | 1.25 | 1.5 | 2 | 2.5 | 3 | 4 |
| Sodium metabisulfite | | | | 0.3 | | | | |
| Dipropylene glycol | | | | 6 | | | | |
| Hydroquinone | | | | 4 | | | | |
| Distilled water | | | up to 100 | | | | | |

Afterwards, the stability over time was observed at 60° C., which is a somewhat severe condition, and the results are shown in FIG. 9. As shown in the FIG. 9, the compositions having 2.5 to 6% by weight of poloxamer were stable until 6 weeks, and the stability of the hydroquinone was better in the compositions having 2.5 to 5% by weight of poloxamer when used until 12 weeks or more. However, because these results are the results under the severe conditions, the results shows that the compositions having other contents may also have sufficient distribution stability under the room temperature.

The invention claimed is:

1. A composition comprising hydroquinone or a derivative thereof as an active ingredient and a poloxamer as a stabilizer,
    wherein the poloxamer is a combination of a first poloxamer and a second poloxamer,
    wherein the first poloxamer has a PPO molecular weight of 1200-1800 g/mol and a PEO content percentage of 30-80%, and the second poloxamer has a PPO molecular weight of 3000-4500 g/mol and a PEO content percentage of 30-80%,
    wherein the hydroquinone derivative is hydroquinone monobenzyl ether, hydroquinone monomethyl ether, hydroquinone monoethyl ether or a mixture thereof, and
    wherein the first poloxamer is poloxamer 188 and the second poloxamer is poloxamer 338, poloxamer 407 or a mixture thereof;
    wherein the hydroquinone or the derivative concentration is of 4 wt. % to less than 10 wt. % based on the total weight of the composition; and
    wherein the combined poloxamer concentration is up to 20 wt. % based on the total weight of the composition.

2. The composition of claim 1, wherein the composition comprises poloxamer micelles, and the external phase of the micelles is a water phase.

3. The composition of claim 1, wherein the composition is for improving whitening.

4. The composition of claim 1, wherein the composition further comprises an antioxidant.

5. The composition of claim 1, wherein the first poloxamer and the second poloxamer are used in a weight ratio of 1:0.1 to 10.

6. The composition of claim 1, wherein the composition further comprises a hydrophilic solvent selected from the group consisting of polyethylene glycol, propylene glycol, dipropylene glycol, glycerin, 1,3-butanediol, isopropyl alcohol, and ethanol.

7. A method of stabilizing hydroquinone or a derivative thereof in a composition comprising hydroquinone or a derivative thereof, comprising adding a poloxamer in the composition,
    wherein the poloxamer is a combination of the first poloxamer and the second poloxamer, the first poloxamer has the PPO molecular weight of 1200-1800 g/mol and the PEO content percentage of 30-80%, and the second poloxamer has the PPO molecular weight of 3000-4500 g/mol and the PEO content percentage of 30-80%,
    wherein the hydroquinone derivative is hydroquinone monobenzyl ether, hydroquinone monomethyl ether, hydroquinone monoethyl ether or a mixture thereof,
    wherein the first poloxamer is poloxamer 188 and the second poloxamer is poloxamer 338, poloxamer 407 or a mixture thereof, and
    wherein the hydroquinone or the derivative concentration is of 4 wt. % to less than 10 wt. % based on the total weight of the composition; and
    wherein the total poloxamer is an amount of up to 20 wt. % based on the total weight of the composition.

8. The method of claim 7, wherein the composition comprises poloxamer micelles, and the external phase of the micelles is a water phase.

9. The method of claim 7, wherein the composition is for improving whitening.

10. The method of claim 7, wherein the composition further comprises an antioxidant.

11. The method of claim 7, wherein the first poloxamer and the second poloxamer are used in a weight ratio of 1:0.1 to 10.

12. The method of claim 7, wherein the composition further comprise a hydrophilic solvent selected from polyethylene glycol, propylene glycol, dipropylene glycol, glycerin, 1,3-butanediol, isopropyl alcohol, or ethanol.

13. The composition of claim 1, wherein the combined poloxamer concentration is of 2.5%-6%.

* * * * *